(12) United States Patent
Burgoyne et al.

(10) Patent No.: US 6,982,329 B2
(45) Date of Patent: Jan. 3, 2006

(54) PROCESS IMPROVEMENTS IN STEROID CHEMISTRY

(75) Inventors: David L. Burgoyne, Delta (CA); Gueijun Ji, Richmond (CA); Eugene W. Kelleher, Arlington, MA (US); Nicholas D. Paschalides, Marlborough, MA (US); Kishore Ramachandran, Burlington, MA (US); Yaping Shen, Port Coquitlam (CA); Yuanlin Zhou, Richmond (CA)

(73) Assignee: Inflazyme Pharmaceuticals Ltd., Richmond (CA)

( * ) Notice: Subject to any disclaimer, the term of this patent is extended or adjusted under 35 U.S.C. 154(b) by 0 days.

(21) Appl. No.: 10/744,857

(22) Filed: Dec. 22, 2003

(65) Prior Publication Data

US 2004/0138486 A1    Jul. 15, 2004

Related U.S. Application Data

(62) Division of application No. 10/154,432, filed on May 22, 2002, now Pat. No. 6,696,580.
(60) Provisional application No. 60/293,013, filed on May 22, 2001.

(51) Int. Cl.
*C07J 21/00* (2006.01)
*C07J 11/00* (2006.01)

(52) U.S. Cl. .......................................... 540/31; 552/612
(58) Field of Classification Search ................... 540/31; 552/612
See application file for complete search history.

(56) References Cited

U.S. PATENT DOCUMENTS 5,869,709 A * 2/1999 Marwah et al. ............. 552/615
6,046,185 A   4/2000 Burgoyne et al. ........... 514/178
6,252,119 B1 * 6/2001 Salvador et al. ............ 568/342

FOREIGN PATENT DOCUMENTS

WO    WO 98/02450     1/1998
WO    WO 01/83512     11/2001

OTHER PUBLICATIONS

Salvador et al., "Copper–Catalysed Allylic Oxidation of 5–ene–Steroids by t–butyl Hydroperoxide.", Tetrahedron Letters, vol. 38(1), pp. 119–122, 1997.*

Brown et al., "Hydroboration. XXVI. The hydroboration of 2–Butenyl (Crotyl) and related derivatives containing representative substituents. Control of the elimination reaction of α–substituted organoboranes," *Journal of the American Chemical Society* 90(11):2906–2915, May 22, 1968.

Jung et al., "First total synthesis of estobergsterol A and active structural analogues of the xestobergsterols," *Tetrahedron* 57(8):1449–1481, Feb. 18, 2001.

Krafft et al., "Synthesis of the C/D/E and A/B rings of Xestobergsterol–(A)" *Journal of Organic Chemistry* 64(7):2475–2485, 1999.

Neves et al., "Improved syntheses of aromatase inhibitors and neuroactive steroids efficient oxidations and reductions at key positions for bioactivity," *Tetrahedron* 55(11):3255–3264, Mar. 1999.

Salvador et al., "Copper–catalysed allylic oxidation of δ–5–steroids by t–butyl–hydroperoxide," *Tetrahedron Letters* 38 (1):119–122, 1997.

Dauben et al. "Allylic Oxidation of Olefins with Chromium Trioxide–Pyridine Complex," *Journal of Organic Chemistry* 34 (11):3587–3592, Nov. 1969.

Jerry March, *Advanced Organic Chemistry: Reactions, Mechanisms, and Structure*, $4^{th}$ Ed., John Wiley & Sons, New York, 1992, Chap. 5–12 & 5–13, pp. 783–790.

Jerry March, *Advanced Organic Chemistry: Reactions, Mechanisms, and Structure*, $4^{th}$ Ed., John Wiley & Sons, New York, 1992, Chap. 5–35, pp. 822–825.

Jerry March, *Advanced Organic Chemistry: Reactions, Mechanisms, and Structure*, $4^{th}$ Ed., John Wiley & Sons, New York, 1992, Chap. 19, "Oxidations and Reductions", pp. 1158–1238.

Miller et al. "A Ruthenium Catalyzed Oxidation of Steroidal Alkenes to Enones," *Tetrahedron Letters* 37(20):3429–3432, 1996.

* cited by examiner

*Primary Examiner*—Barbara P. Badio
(74) *Attorney, Agent, or Firm*—Seed IP Law Group PLLC

(57) ABSTRACT

Steroids containing a cyclohexene moiety are efficiently oxidized to the corresponding α,β-unsaturated ketone using copper iodide and t-butyl hydroperoxide. A steroid compound containing the α,β-unsaturated ketone structure is efficiently converted to the corresponding vicinal diol using a hydroborating reagent followed by oxidative workup, e.g., borane followed by sodium perborate. Benzoyl and substituted benzoyls are superior protecting groups for hydroxyl groups present in the compounds.

20 Claims, 1 Drawing Sheet

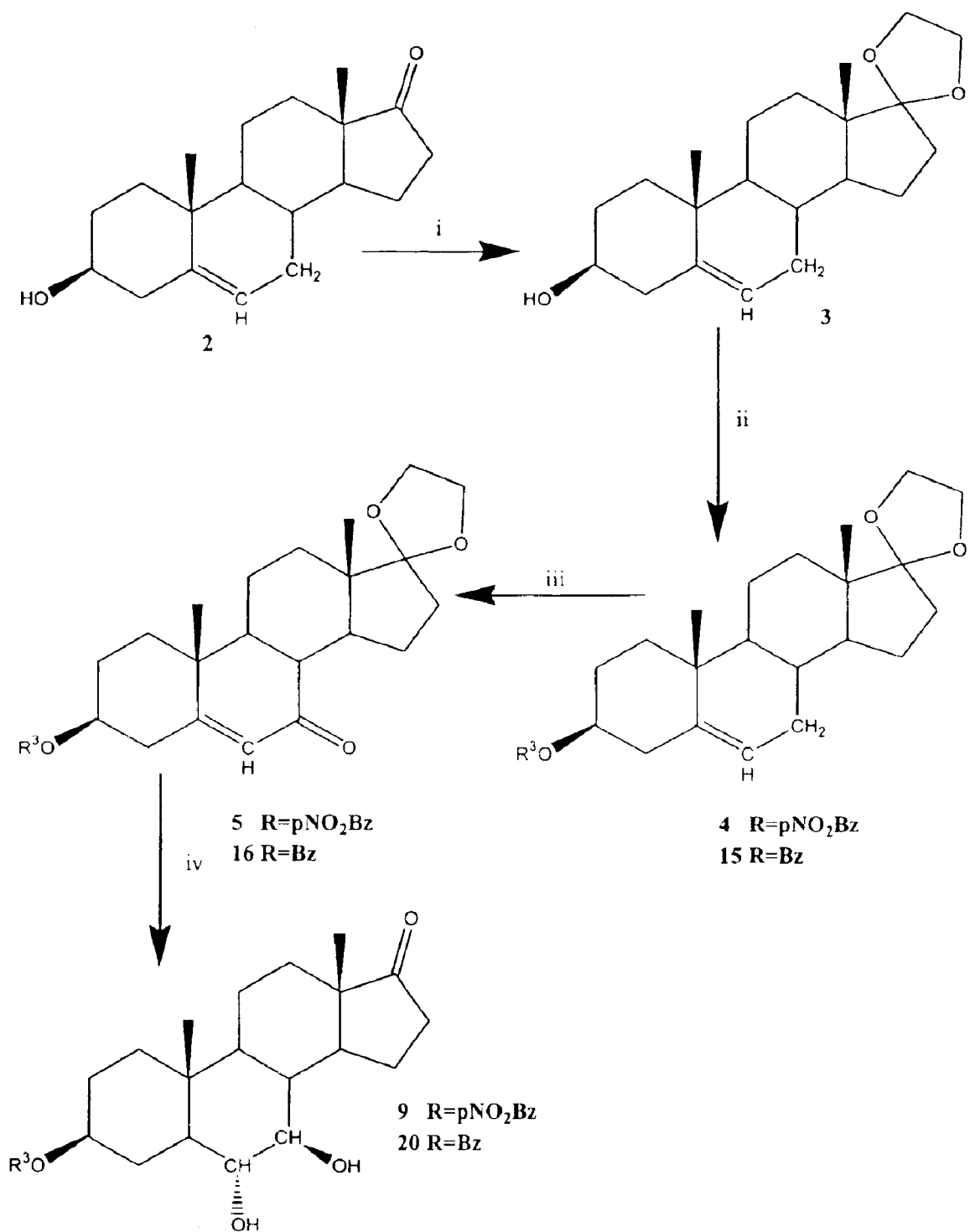
FIG.

PROCESS IMPROVEMENTS IN STEROID CHEMISTRY

CROSS-REFERENCE TO RELATED APPLICATION

This application is a divisional of U.S. patent application Ser. No. 10/154,432 filed May 22, 2002 now U.S. Pat. No. 6,696,580, now allowed, which application claims the benefit of U.S. Provisional Patent Application No. 60/293,013 filed May 22, 2001, which applications are incorporated herein by reference in their entireties.

BACKGROUND OF THE INVENTION

1. Field of the Invention

The present invention is directed to synthetic manipulations of organic chemicals, and particularly to the chemical reactions of steroids, and to steroids that may be used as starting materials in various chemical reactions, and to steroids that result from the chemical reactions.

2. Description of the Related Art

Steroid structures are commonly used as therapeutic agents. See, e.g., PCT International Publication No. WO 98/02450 and U.S. Pat. No. 6,046,185, among many other documents that discuss the therapeutic efficacy of steroids. Accordingly, there is a need in the art for efficient synthetic reactions that can prepare steroids of a desired structure. The present invention is directed to fulfilling this and related needs as described in detail herein.

BRIEF SUMMARY OF THE INVENTION

The present invention provides general synthetic methodology that may be employed to prepare steroid compounds having certain specified chemical functionality.

In one aspect, the present invention provides a method for allylic oxidation comprising a) providing a compound comprising a steroid carbon skeleton and two geminal allylic hydrogens as present in formula (1)

(1)

b) contacting the compound with reagents comprising copper iodide and t-butyl hydroperoxide to provide a mixture; and c) maintaining the mixture of step b) under oxidizing conditions to convert the compound to a product having a carbon skeleton and an α,β-unsaturated ketone moiety as present in formula (4)

(4)

In a separate aspect, the present invention provides another method for allylic oxidation comprising a) providing a compound comprising a steroid carbon skeleton and two geminal allylic hydrogens as present in formula (1)

(1)

b) contacting the compound with reagents comprising an oxidizing agent and an amine to provide a mixture;

c) maintaining the mixture of step b) under oxidizing conditions to convert the compound to a product having a carbon skeleton and an α,β-unsaturated ketone moiety as present in formula (4)

(4)

In another aspect, the present invention provides a method of converting a compound having a steroid carbon nucleus and an enone (i.e., an α,β-unsaturated ketone moiety), as may be prepared by the just-described allylic oxidation method, to a compound having a steroid carbon nucleus and two hydroxyl groups (i.e., a diol), one at the 6-position and the other at the 7-position of the steroid nucleus.

Thus, in one aspect the present invention provides a method of converting an enone to a diol, comprising a) providing a compound comprising a steroid carbon skeleton and an α,β-unsaturated ketone moiety as present in a compound of formula (4)

(4)

b) contacting the compound of a) with a hydroborating agent e.g., borane, bis-3-methyl-2-butylborane (disamylborane) or 9-borabicylo[3.3.1]nonane (9-BBN), preferably in an ethereal solvent such as tetrahydrofuran, to form a hydroboration product, followed by an oxidative workup, e.g., contacting the hydroboration product with perborate salt ($NaBO_3$), or $NaOH/H_2O_2$;

c) forming a product comprising a steroid carbon skeleton and two hydroxyl groups as present in a compound of formula (5)

(5)

In addition, the present invention provides steroid compounds.

In one aspect, the present invention provides a compound of the formula wherein:

Z is selected from O, S, and N—$R^1$;

each of C1, C2, C4, C11, C12, C15, C16 and C17 is independently substituted with (a) one of: =O, =C($R^1$)($R^1$), —C($R^1$)($R^1$)(C($R^1$)($R^1$))$_n$— and —(O(C($R^1$)($R^1$))$_n$O)— wherein n ranges from 1 to about 6; or (b) two of the following, which are independently selected: —X, —$R^1$ and —$OR^2$;

each of C8, C9 and C14 is independently substituted with one of —X, —$R^1$ or —$OR^2$;

C7 is substituted with two hydrogens, oxo, hydrogen and hydroxyl, or hydrogen and protected hydroxyl;

$R^1$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded; and $R^2$ is H or a protecting group such that —$OR^2$ is a protected hydroxyl group, where vicinal —$OR^2$ groups may together form a cyclic structure which protects vicinal hydroxyl groups, and where geminal —$OR^2$ groups may together form a cyclic structure which protects a carbonyl group;

$R^3$ is benzoyl or substituted benzoyl; and

X is fluoride, chloride, bromide and iodide.

In another aspect, the present invention provides a compound of the formula wherein:

Z is selected from O, S, and N—$R^1$;

each of C1, C2, C4, C11, C12, C15, C16 and C17 is independently substituted with (a) one of: =O, =C($R^1$)($R^1$), —C($R^1$)($R^1$)(C($R^1$)($R^1$))$_n$— ba and —(O(C($R^1$)($R^1$))$_n$O)— wherein n ranges from 1 to about 6; or (b) two of the following, which are independently selected: —X, —$R^1$ and —$OR^2$;

each of C5, C8, C9 and C14 is independently substituted with one of —X, —$R^1$ or —$OR^2$;

$R^1$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded; and $R^2$ is H or a protecting group such that —$OR^2$ is a protected hydroxyl group, where vicinal —$OR^2$ groups may together form a cyclic structure which protects vicinal hydroxyl groups, and where geminal —$OR^2$ groups may together form a cyclic structure which protects a carbonyl group;

$R^3$ is benzoyl or substituted benzoyl; and

X is fluoride, chloride, bromide and iodide.

The compounds of the present invention are useful as intermediates in the preparation of steroids having medicinal properties. Synthetic methodology as described herein may be utilized to prepare compounds of the present invention.

These and related aspects of the present invention are disclosed in further detail herein.

BRIEF DESCRIPTION OF THE DRAWING

The FIGURE shows a synthetic scheme wherein compounds of the invention are prepared by methods of the invention. In the FIGURE, $R^3$ in compounds 4, 5, and 9 is para-nitrobenzoyl, while $R^3$ in compounds 15, 16 and 20 is benzoyl. In the FIGURE, step i. shows the protection of a C17 carbonyl group, step ii. shows the protection of a C3 hydroxyl group; step iii. shows the conversion of an allyl moiety to an α,β-unsaturated ketone moiety, and step iv shows the conversion of an α,β-unsaturated ketone moiety to a vicinal diol.

DETAILED DESCRIPTION OF THE INVENTION

Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

Benzoyl is —(C=O)-Ph where "Ph" represents phenyl. Substituted benzoyl refers to a benzoyl group wherein one or more of the phenyl hydrogens is replaced with a substituent selected from hydroxyl, alkoxy, aryloxy, haloalkoxy, cyano, nitro, mercapto, alkylthio, —N=N—O—$R^5$, —N($R^4$)$_2$, —C(O)O$R^4$, —C(O)N($R^4$)$_2$ or —N($R^4$)C(O)$R^4$ where each $R^4$ is independently hydrogen, alkyl, alkenyl, cycloalkyl, cycloalkylalkyl, aralkyl or aryl, and $R^5$ is hydrogen, alkyl or aralkyl. In one aspect of the invention, substituted benzoyl is para-nitrobenzoyl, optionally referred to herein as p-nitrobenzoyl or p-$NO_2$Bz.

Protecting groups for hydroxyl, thiol, and amino groups, including methods to add such protecting groups to an unprotection functional group, and further including methods to remove the protecting group, where these protecting groups are designated herein as $R^2$ and/or $R^3$, are well known in the art. See, e.g., Greene, T. W. and Wuts, P. G. M., Protective Groups in Organic Synthesis, Wiley, New York, N.Y. (1991).

Allylic Oxidation

In one aspect, the present invention provides for the allylic oxidation of a unsaturated (i.e., olefin-containing) steroid compound having two hydrogen atoms at an allylic position as shown in formula (1), where only the carbon skeleton of the steroid is shown in formula (1), and with the exception of the allylic hydrogens and a site of unsaturation, any substitution on the carbon skeleton is omitted for clarity.

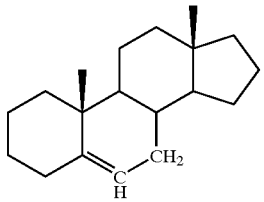

(1)

In one embodiment, the present invention provides for the allylic oxidation of a steroid of formula (1), where the method comprises:

a) providing a steroid compound having two allylic hydrogens and comprising the carbon nucleus as shown in formula (1)

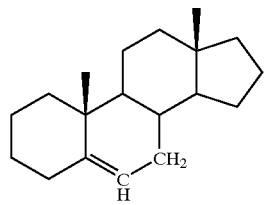

(1)

b) contacting the compound with reagents comprising copper iodide and t-butyl hydroperoxide to provide a mixture; and c) maintaining the mixture of step b) under oxidizing conditions to convert the steroid structure to a steroid having the carbon nucleus and an α,β-unsaturated ketone moiety as shown in formula (4)

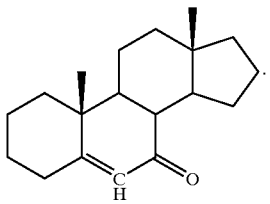

(4)

A series of experiments were run to test both the effect of solvent and catalyst on yields of the allylic oxidation reaction. Selected examples of these reactions are summarized in Tables 1 and 2, where compounds 4 and 15 are identified in the FIGURE. In these Tables, ACN represents acetonitrile, BuOOH represents t-butyl hydroperoxide, CuI represents copper iodide, DCM represents dichloromethane, g represents gram(s), SM represents starting material (see the FIGURE, and in particular compound 3), T represents temperature, and v/v represents volume/volume ratio.

In general, using CuI as a catalyst, the following conditions were found to be optimal:
1. 0.02:1 mole ratio of CuI catalyst to starting material.
2. approximately 10:1 mole ratio of tBuOOH to starting material.
3. approximately 1:1:0.3 vol ratio of ACN/Cyclohexane/Pyridine for the benzoate starting material.
4. approximately 1:1:0.5 ACN/DCM/Pyridine for the para-nitro benzoate starting material.
5. temperature maintained at approximately 40° C.–50° C.

TABLE 1

CuI catalyzed allylic oxidation of compound 15

| Entry No. | Amt. of Starting Material (SM) | Mol. Ratio: BuOOH/SM | Mol. Ratio: CuI/SM | Yield (%) | Solvent (v/v) | T (° C.) | Comments |
|---|---|---|---|---|---|---|---|
| 1. | 5.0 g | 12.6 | 0.02 | 43.8 | DCM/ACN (1/1) | 50 | Significant amount of by-product was formed |
| 2. | 1.0 g | 10 | 0.02 | 60.7 | DCM/ACN/pyridine (1/1/0.3) | 50 | |
| 3. | 5.0 g | 10 | 0.02 | 69.2 | ACN/cyclohexane/pyridine (1/1/0.3) | 45 | |
| 4. | 5.0 g | 10 | 0.02 | 64.5 | DCM/ACN/pyridine (1/1/0.3) | 45 | |
| 5. | 5.0 g | 10 | 0.02 | 67.7 | DCM/pyridine (1/0.25) | 40 | |

TABLE 1-continued

CuI catalyzed allylic oxidation of compound 15

| Entry No. | Amt. of Starting Material (SM) | Mol. Ratio: BuOOH/SM | Mol. Ratio: CuI/SM | Yield (%) | Solvent (v/v) | T (° C.) | Comments |
|---|---|---|---|---|---|---|---|
| 6. | 50.0 g | 10 | 0.02 | 64.3 | ACN/cyclohexane/pyridine (1/1/0.3) | 50 | |

TABLE 2

CuI catalyzed allylic oxidation of compound 4

| Entry No. | Amt. of Starting Material (SM) | Mole ratio: BuOOH/SM | Mole ratio CuI/SM | Yield | Conditions | Solvent - (v/v) |
|---|---|---|---|---|---|---|
| 1. | 5.0 g | 10/1.0 | 0.02/1.0 | 57.86 | 50° C., overnight | Cyclohexane/ACN - (1/1) |
| 2. | 5.0 g | 13/1.0 | 0.01/1.0 | 51.65 | 50° C., overnight | Cyclohexane/ACN - (1/1) |
| 3. | 5.0 g | 13/1.0 | 0.02/1.0 | 54.34 | Reaction done by 9 hr at 50° C. | Cyclohexane/ACN - (1/1) |
| 4. | 5.0 g | 13/1.0 | 0.02/1.0 | 53.4 | Reaction done by 3 hr at 75° C. | Cyclohexane/ACN - (1/1) |
| 5. | 5.0 g | 13/1.0 | 0.02/1.0 | 64.0 | Reaction done by 5 hr at 50° C. | Cyclohexane/ACN/pyridine - (1/1/0.5) |
| 6. | 5.0 g | 10/1.0 | 0.02/1.0 | 57.17 | Reaction done by 2 hr at 65° C. | Cyclohexane/ACN/pyridine - (1/1/0.5) |
| 7. | 5.0 g | 7.0/1.0 | 0.02/1.0 | 24.3 | 50° C., overnight | Cyclohexane/ACN/pyridine - (1/1/0.5) |
| 8. | 5.0 g | 10/1.0 | 0.02/1.0 | 62.14 | 50° C., 2 hr | DCM/pyridine - (1/0.5) |
| 9. | 5.0 g | 10/1.0 | 0.02/1.0 | 61.0 | 50° C., 2 hr | DCM/ACN/pyridine - (1/1/0.75) |
| 10. | 5.0 g | 7.0/1.0 | 0.02/1.0 | 58.25 | 50° C., 2 hr | DCM/pyridine - (1/0.75) |
| 11. | 5.0 g | 7.0/1.0 | 0.01/1.0 | 48.0 | 50° C., 4 hr | DCM/pyridine - (1/0.75) |
| 12. | 5.0 g | 10/1.0 | 0.02/1.0 | 66.9 | 50° C., 2 hr | DCM/ACN/pyridine - (1/1/0.5) |
| 13. | 1.0 g | 10/1.0 | 0.02/1.0 | 62.0 | 50° C., 4 hr | DCM/ACN/pyridine - (1/1/0.25) |

A specific steroid within the scope of formula (1) that may be used in the allylic oxidation reaction of the present invention has the formula (2):

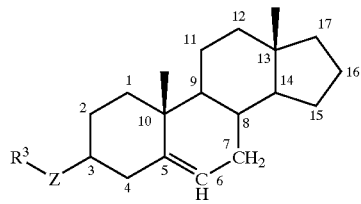

(2)

wherein:

Z is selected from O, S, and N—$R^1$;

each of C1, C2, C3, C4, C11, C12, C15, C16 and C17 is independently substituted with
  a) one of: =O, =C($R^1$)($R^1$), —C($R^1$)($R^1$)(C($R^1$)($R^1$))$_n$— and —(O(C($R^1$)($R^1$))$_n$O)— wherein n ranges from 1 to about 6; or
  b) two of the following, which are independently selected: —X, —$R^1$ and —$OR^2$;

each of C8, C9 and C14 is independently substituted with one of —X, —$R^1$ or —$OR^2$;

$R^1$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded;

$R^2$ is H or a protecting group such that —$OR^2$ is a protected hydroxyl group, where vicinal —$OR^2$ groups may together form a cyclic structure which protects vicinal hydroxyl groups, and where geminal —$OR^2$ groups may together form a cyclic structure which protects a carbonyl group, with the proviso that either or both of —$OR^2$ at C6 and C7 represents a carbonyl or protected carbonyl group; and X represents fluoride, chloride, bromide and iodide.

In particular embodiments, C1, C2, C4, C11, C12, C15 and C16 are substituted with two hydrogens, and C8, C9 and C14 are substituted with one hydrogen; and/or C3 is substituted with hydrogen and —$OR^2$, and/or C17 is substituted with two —$OR^2$ groups or a ketal. In another particular embodiment of the invention, the steroid has the formula (3) wherein each carbon is hydrogen-substituted unless otherwise indicated, Z is selected from O, S and N$R^1$, and wherein $R^3$ is a protecting group for Z

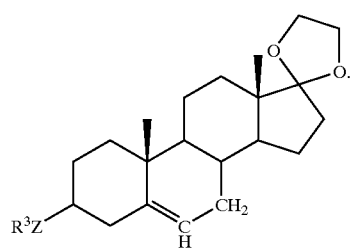

(3)

In one embodiment of steroids of formula (3), $R^3$ is para-nitrobenzoyl. In one embodiment $R^3$ is para-nitrobenzoyl where -Z$R^3$ is only or primarily in the beta-configuration (i.e., up, out of the plane of the steroid, as are the two methyl groups shown in formula (3)), i.e., the steroid may be compound 4 in the FIGURE where Z is O. In one embodiment $R^3$ is para-nitrobenzoyl where $-ZR^3$ is only or primarily in the alpha-configuration (i.e., down, below the plane of the steroid, opposite to the configuration of the two methyl groups shown in formula (3)). In one aspect of this embodiment, Z is O. In another aspect of this embodiment, Z is S. In another aspect of this embodiment, Z is $NR^1$ where $R^1$ is defined above, and where a preferred $R^1$ is selected from an amino protecting group and H, i.e., $R^1$ in the group $-NR^1$ is preferably $R^3$ so that $-ZR^3$ is $N(R^3)_2$ or H so that $-ZR^3$ is $-NHR^3$.

In another embodiment of steroids of formula (3), $R^3$ is benzoyl. In one embodiment $R^3$ is benzoyl where $-ZR^3$ is only or primarily in the beta-configuration (i.e., up, out of the plane of the steroid, as are the two methyl groups shown in formula (3)), i.e., the steroid may be compound 15 in the FIGURE where Z is O. In one embodiment $R^3$ is benzoyl where $-OR^3$ is only or primarily in the alpha-configuration (i.e., down, below the plane of the steroid, opposite to the configuration of the two methyl groups shown in formula (3)). In one aspect of this embodiment, Z is O. In another aspect of this embodiment, Z is S. In another aspect of this embodiment, Z is $NR^1$ where $R^1$ is defined above, and where a preferred $R^1$ is selected from an amino protecting group and H, i.e., $R^1$ in the group $-NR^1$ is preferably $R^3$ so that $-ZR^3$ is $N(R^3)_2$ or H so that $-ZR^3$ is $-NHR^3$.

Thus, in one aspect, the olefin-containing steroid compound is compound 4 where $-ZR^3$ is $-OR^3$, and $-OR^3$ is only or primarily in the beta-configuration, while in another aspect the olefin-containing compound is compound 15 where $-ZR^3$ is $-OR^3$, and $-OR^3$ is only or primarily in the beta-configuration.

In the oxidation reaction, and in particular with respect to the solvent, it is observed in Tables 1 and 2 that the oxidation reaction works in the majority of solvents tested. Reduction of the catalyst to 0.01 resulted in significantly reduced yields. Temperatures of higher than 45° C. (for the benzoate) and 50° C. (for the para-nitrobenzoate) resulted in reduced yields. A ten fold excess of tBuOOH was observed to maximize yields.

Many solvent systems may be used in the oxidation reaction, however specific systems are preferred depending on the protecting group at the C3 position. For example, the 1:1:0.3 cyclohexane/acetonitrile/pyridine mixture provided the most consistent yields for the starting material with the benzoyl protecting group, whereas the 1:1:0:5 ACN/DCM/Pyridine solvent system is preferred for the starting material with the para-nitrobenzoyl protecting group. Accordingly, in one aspect of the invention, the oxidation reaction is conducted in the further presence of an amine, e.g., pyridine or a tertiary amine such as 1,4-diazabicyclo[2.2.2]octane (DABCO). Specifically, the addition of amine reduces the variability and increases yields compared to reactions run in the absence of amine.

Thus, in another embodiment, the present invention provides for the allylic oxidation of steroid of formula (1), where the method comprises:

a) providing a compound comprising a steroid carbon nucleus, unsaturation between carbons 5 and 6, and two allylic hydrogens as shown in formula (1)

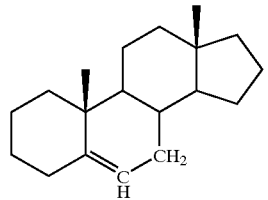

(1)

b) contacting the compound with reagents that comprise an oxidizing agent and an amine to provide a mixture; and c) maintaining the mixture of step b) under oxidizing conditions to convert the cyclohexene structure to an α,β-unsaturated ketone of the formula (4)

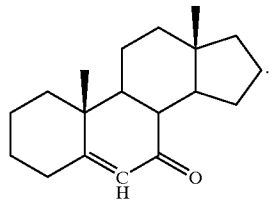

(4)

In one aspect, the oxidizing agent is copper iodide and t-butyl hydroperoxide. In another aspect, the oxidizing agent is ruthenium chloride ($RuCl_3$) and t-butyl hydroperoxide. Optionally, the amine is selected from tertiary amines and pyridine.

A particular steroid of formula (1) that may be used in this oxidation reaction is a compound having the formula (2) as identified above. In particular embodiments, C1, C2, C4, C11, C12, C15 and C16 are substituted with two hydrogens, and C8, C9 and C14 are substituted with one hydrogen; and/or C3 is substituted with hydrogen and $-OR^2$, and C17 is substituted with two $-OR^2$ groups or a ketal. In another particular embodiment of the invention, the steroid has the formula (3) as identified above, wherein each carbon is hydrogen-substituted unless otherwise indicated, and wherein $R^3$ is a protecting group.

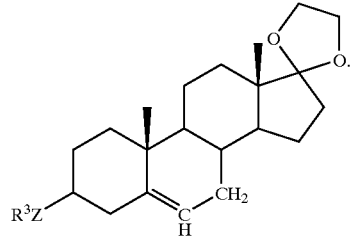

(3)

In one embodiment of steroids of formula (3), $R^3$ is para-nitrobenzoyl. In one embodiment $R^3$ is para-nitrobenzoyl where $-OR^3$ is only or primarily in the beta-configuration (i.e., up, out of the plane of the steroid, as are the two methyl groups shown in formula (3)), i.e., the steroid is compound 4 in the FIGURE. In one embodiment $R^3$ is para-nitrobenzoyl where $-OR^3$ is only or primarily in the alpha-configuration (i.e., down, below the plane of the steroid, opposite to the configuration of the two methyl groups shown in formula (3)). In one aspect of this embodiment, Z is O. In another aspect of this embodiment, Z is S. In another aspect of this embodiment, Z is $NR^1$ where $R^1$ is defined above, and where a preferred $R^1$ is selected from an amino protecting group and H, i.e., $R^1$ in the group —$NR^1$ is preferably $R^3$ so that -$ZR^3$ is $N(R^3)_2$ or H so that -$ZR^3$ is —$NHR^3$.

In one embodiment, $R^3$ is benzoyl. In one embodiment $R^3$ is benzoyl where —$OR^3$ is only or primarily in the beta-configuration (i.e., up, out of the plane of the steroid, as are the two methyl groups shown in formula (3)), i.e., the steroid is compound 15 in the FIGURE. In one embodiment $R^3$ is benzoyl where —$OR^3$ is only or primarily in the alpha-configuration, (i.e., down, below the plane of the steroid, opposite to the configuration of the two methyl groups shown in formula (3)). In one aspect of this embodiment, Z is O. In another aspect of this embodiment, Z is $NR^1$ where $R^1$ is defined above, and where a preferred $R^1$ is selected from an amino protecting group and H, i.e., $R^1$ in the group —NR is preferably $R^3$ so that -$ZR^3$ is $N(R^3)_2$ or H so that -$ZR^3$ is —$NHR^3$.

Thus, in one aspect, the olefin-containing steroid compound is compound 4 where -$ZR^3$ is —$OR^3$, and —$OR^3$ is exclusively or primarily in the beta-configuration, while in another aspect the olefin-containing compound is compound 15 where -$ZR^3$ is —$OR^3$, and —$OR^3$ is exclusively or primarily in the beta-configuration.

Conversion of Enone Group to Diol Group

In another aspect, the present invention provides a method of converting an enone to a diol. The enone-containing compound, which may also be referred to as an α,β-unsaturated ketone-containing compound, is generally represented by formula (4)

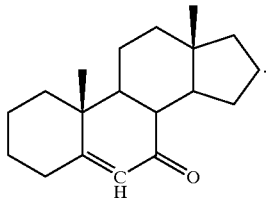

(4)

where the carbon skeleton of the steroid is shown in formula (4) and, with the exception of the carbonyl group at carbon 7 and a site of unsaturation between carbons 5 and 6, any other substitution on the carbon skeleton is omitted for purposes of clarity. The product diol is generally represented by formula (5)

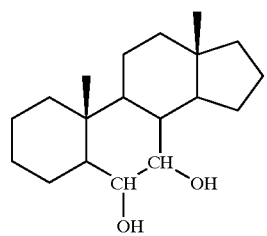

(5)

where again the carbon skeleton of the steroid is shown in formula (5) and, with the exception of the two hydroxyl groups at carbons 6 and 7, any substitution on the carbon skeleton is omitted for clarity.

Thus, the present invention provides a method of converting a steroid containing an enone group to the corresponding steroid containing a vicinal diol group at the 6 and 7 positions of the steroid, where the method includes:

a) providing a steroid compound having the carbon skeleton and enone structure

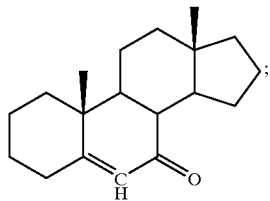

(4)

b) contacting the compound of a) with a hydroboration reagent to form a hydroboration product, followed by an oxidative work-up; and c) forming a product comprising a steroid carbon skeleton and hydroxyl functionality of the formula (5)

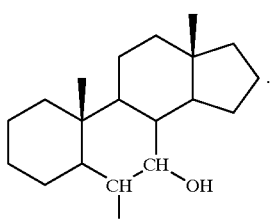

(5)

In various embodiments of this aspect of the invention, step b) includes contacting the compound with borane; and/or contacting the compound with a hydroborating agent selected from bis-3-methyl-2-butylborane or 9-borabicyclo[3.3.1]nonane; and/or the oxidative workup of b) comprises adding $NaBO_3$ to the hydroboration product; and/or the oxidative workup of b) comprises adding NaOH and $H_2O_2$ to the hydroboration product. As used herein, the term "borane" refers to any of $BH_3$, $B_2H_6$ (sometimes also referred to as diborane), higher-order borane-borane complexes (e.g., $(BH_3)_n$ where n is 1–6), as well as solvated forms thereof, e.g., ethereal complexes such as $BH_3.THF$ (also referred to as $BH_3/THF$).

Preferably step b) is conducted without isolation of the hydroboration product, that is, after the compound has been combined with the hydroboration reagent, the product of this hydroboration reaction is subjected to oxidative workup conditions without any isolation of the hydroboration product. Hydroboration followed by an oxidative work-up is well known in the art, and is described in, e.g., Carey and Sundberg, Advanced Organic Chemistry, 3$^{rd}$ Edition, 1990, Plenum Press; and March, Advanced Organic Chemistry, 4$^{th}$ Edition, 1992, Wiley-Interscience, see particularly pp. 783–789.

In addition, in one aspect, the compound is added to a reaction vessel containing the hydroborating agent. In a different aspect, the hydroborating agent is added to a reaction vessel containing the compound.

A particular steroid that may be used in converting a steroid containing an enone group according to formula (4)

to a diol according to formula (5) is a compound having the formula

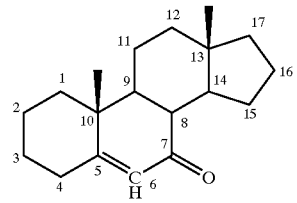

wherein:

each of C1, C2, C3, C4, C11, C12, C15, C16 and C17 is independently substituted with a) one of =O, =C(R$^1$)(R$^1$), —C(R$^1$)(R$^1$)(C(R$^1$)(R$^1$))$_n$— and —(O(C(R$^1$)(R$^1$))$_n$O)— wherein n ranges from 1 to about 6; or b) two of the following, which are independently selected: —X, —R$^1$ and —OR$^2$;

each of C8, C9 and C14 is independently substituted with one of —X, —R$^1$ or —OR$^2$;

R$^1$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^1$ groups may together form a ring with the carbon atom to which they are both bonded;

R$^2$ is H or a protecting group such that —OR$^2$ is a protected hydroxyl group, where vicinal —OR$^2$ groups may together form a cyclic structure which protects vicinal hydroxyl groups, and where geminal —OR$^2$ groups may together form a cyclic structure which protects a carbonyl group, with the proviso that either or both of —OR$^2$ at C6 and C7 represents a carbonyl or protected carbonyl group; and X represents fluoride, chloride, bromide and iodide.

According to this embodiment of the invention, the product diol has the corresponding formula

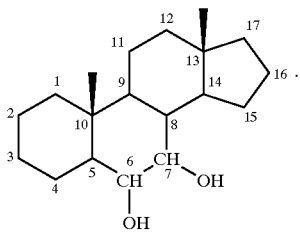

In more specific aspects of the invention C1, C2, C4, C11, C12, C15 and C16 are substituted with two hydrogens, and C8, C9 and C14 are substituted with one hydrogen, and/or C3 is substituted with hydrogen and —OR$^2$, and/or C17 is substituted with two —OR$^2$ groups or a ketal. In one particular embodiment, the steroid of formula (4) may be represented by formula (6) wherein each carbon is hydrogen-substituted unless otherwise indicated, Z is selected from O, S and NR$^1$, and wherein R$^3$ is a protecting group for Z

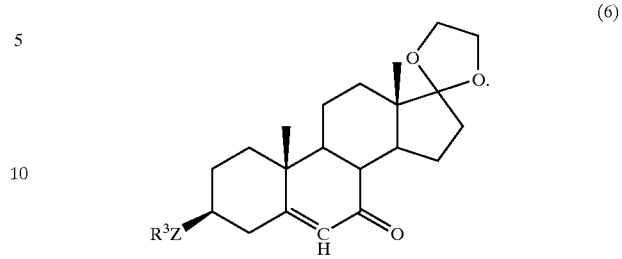

In one embodiment of steroids of formula (6), R$^3$ is para-nitrobenzoyl. In one embodiment R$^3$ is para-nitrobenzoyl where -ZR$^3$ is exclusively or primarily in the beta-configuration (i.e., up, out of the plane of the steroid, as are the two methyl groups shown in formula (6), i.e., the steroid may be compound 5 in the FIGURE when Z is O. In one embodiment R$^3$ is para-nitrobenzoyl where -ZR$^3$ is exclusively or primarily in the alpha-configuration, (i.e., down, below the plane of the steroid, opposite to the configuration of the two methyl groups shown in formula (6)). In one aspect of this embodiment, Z is O. In another aspect of this embodiment, Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

In one embodiment, R$^3$ is benzoyl. In one embodiment R$^3$ is benzoyl where -ZR$^3$ is exclusively or primarily in the beta-configuration (i.e., up, out of the plane of the steroid, as are the two methyl groups shown in formula (6), i.e., the steroid may be compound 16 in the FIGURE when Z is O. In one embodiment R$^3$ is benzoyl where -ZR$^3$ is only or primarily in the alpha-configuration, (i.e., down, below the plane of the steroid, opposite to the configuration of the two methyl groups shown in formula (6)). In one aspect of this embodiment, Z is O. In another aspect of this embodiment, Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

Thus, in one aspect, the enone-containing compound is compound 5 where -ZR$^3$ is —OR$^3$, and —OR$^3$ is exclusively or primarily in the beta-configuration, while in another aspect the enone-containing compound is compound 16 where -ZR$^3$ is —OR$^3$, and —OR$^3$ is exclusively or primarily in the beta-configuration.

Compounds of the Invention

The allylic oxidation reaction described above, and/or the conversion of an enone-containing compound to the corresponding vicinal diol, advantageously utilizes a steroid compound having specific substitution at the 3 position. Thus, in one aspect the present invention provides olefin-containing steroid compounds of the formula

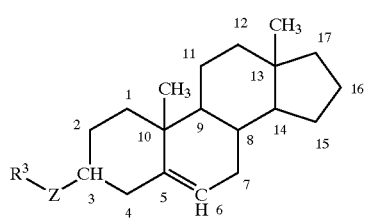

wherein:

Z is O, S or NR$^1$;

each of C1, C2, C4, C11, C12, C15, C16 and C17 is independently substituted with (a) one of: =O, =C(R$^1$)(R$^1$), —C(R$^1$)(R$^1$)(C(R$^1$)(R$^1$))$_n$— and —(O(C(R$^1$)(R$^1$))$_n$O)— wherein n ranges from 1 to about 6; or (b) two of the following, which are independently selected: —X, —R$^1$ and —OR$^2$;

each of C8, C9 and C14 is independently substituted with one of —X, —R$^1$ or —OR$^2$;

C7 is substituted with two hydrogens, oxo, hydrogen and hydroxyl, or hydrogen and protected hydroxyl;

R$^1$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^1$ groups may together form a ring with the carbon atom to which they are both bonded; and R$^2$ is H or a protecting group such that —OR$^2$ is a protected hydroxyl group, where vicinal —OR$^2$ groups may together form a cyclic structure which protects vicinal hydroxyl groups, and where geminal —OR$^2$ groups may together form a cyclic structure which protects a carbonyl group;

R$^3$ is benzoyl or substituted benzoyl; and

X is fluoride, chloride, bromide and iodide.

In various aspects, the steroid compound is as set forth above, however: R$^3$ is nitro-substituted benzoyl; and/or each of C1, C2, C4, C11, C12, C15 and C16 is substituted with two hydrogens; and/or each of C8, C9 and C14 is substituted with one hydrogen; and/or C17 is substituted with a substituent selected from =O, —(O(C(R$^1$)(R$^1$))$_n$O)— wherein n ranges from 1 to about 6, hydrogen and —OR$^2$, and two OR$^2$ groups; and/or C7 is substituted with two hydrogens or oxo. In each of these possible aspects, in a further aspect Z is O, while in a separate aspect Z is S, while in a still further aspect Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

Thus, in one aspect, the steroid compound has a structure according to formula (3) wherein each shown carbon is fully substituted with hydrogen, with the exception of the 5-6 double bond

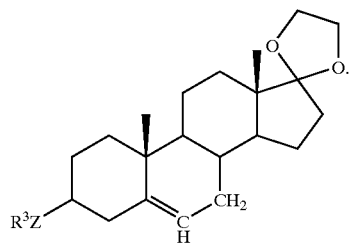

(3)

In one embodiment of steroids of formula (3), R$^3$ is para-nitrobenzoyl, preferably para-nitrobenzoyl. In one embodiment R$^3$ is para-nitrobenzoyl where -ZR$^3$ is exclusively or primarily in the beta-configuration, (i.e., up, out of the plane of the steroid, as are the two methyl groups shown in formula (3)), i.e., the steroid may be compound 4 in the FIGURE when Z is O. In one embodiment R$^3$ is para-nitrobenzoyl where -ZR$^3$ is exclusively or primarily in the alpha-configuration, (i.e., down, below the plane of the steroid, opposite to the configuration of the two methyl groups shown in formula (3)). In one aspect of these embodiments, Z is O. In another aspect of these embodiments, Z is S. In another aspect of these embodiments, Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

In one embodiment, R$^3$ is benzoyl. In one embodiment R$^3$ is benzoyl and R$^3$Z- is exclusively or primarily in the beta-configuration, (i.e., up, out of the plane of the steroid, as are the two methyl groups shown in formula (3)), i.e., the steroid may be compound 15 in the FIGURE when Z is O. In one embodiment R$^3$ is benzoyl and -ZR$^3$ is exclusively or primarily in the alpha-configuration (i.e., down, below the plane of the steroid, opposite to the configuration of the two methyl groups shown in formula (3)). In one aspect of these embodiments, Z is O. In another aspect of these embodiments, Z is S. In another aspect of these embodiments, Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

Thus, in one aspect, the olefin-containing steroid compound is compound 4 where -ZR$^3$ is —OR$^3$, and —OR$^3$ is exclusively or primarily in the beta-configuration, while in another aspect the olefin-containing compound is compound 15 where -ZR$^3$ is —OR$^3$, and —OR$^3$ is exclusively or primarily in the beta-configuration.

Thus, in one aspect, the steroid compound has the structure according to formula (6) wherein each carbon is hydrogen-substituted unless otherwise indicated, Z is selected from O, S and NR$^1$, and wherein R$^3$ is a protecting group for Z, as shown

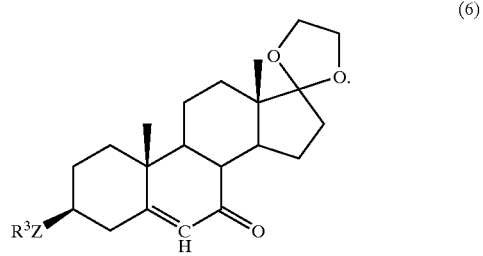

(6)

In one embodiment of steroids of formula (6), R$^3$ is para-nitrobenzoyl. In one embodiment R$^3$ is para-nitrobenzoyl and R$^3$Z- is exclusively or primarily in the beta-configuration (i.e., up, out of the plane of the steroid, as are the two methyl groups shown in formula (6), i.e., the steroid may be compound 5 in the FIGURE when Z is O. In one embodiment R$^3$ is para-nitrobenzoyl and R$^3$Z- is only or primarily in the alpha-configuration (i.e., down, below the plane of the steroid, opposite to the configuration of the two methyl groups shown in formula (6)). In one aspect of these embodiments, Z is O. In another aspect of these embodiments, Z is S. In another aspect of these embodiments, Z is NR$^1$ where R$^1$ is defined above, and where a preferred R$^1$ is selected from an amino protecting group and H, i.e., R$^1$ in the group —NR$^1$ is preferably R$^3$ so that -ZR$^3$ is N(R$^3$)$_2$ or H so that -ZR$^3$ is —NHR$^3$.

In one embodiment, R$^3$ is benzoyl. In one embodiment R$^3$ is benzoyl and R$^3$Z- is exclusively or primarily in the beta-configuration (i.e., up, out of the plane of the steroid, as are the two methyl groups shown in formula (6), i.e., the steroid may be compound 16 in the FIGURE when Z is O. In one embodiment R$^3$ is benzoyl and R$^3$Z- is only or primarily in the alpha-configuration (i.e., down, below the plane of the steroid, opposite to the methyl groups shown in formula (6)). In one aspect of these embodiments, Z is O. In another aspect of these embodiments, Z is S. In another aspect of these embodiments, Z is $NR^1$ where $R^1$ is defined above, and where a preferred $R^1$ is selected from an amino protecting group and H, i.e., $R^1$ in the group —$NR^1$ is preferably $R^3$ so that -$ZR^3$ is $N(R^3)_2$ or H so that -$ZR^3$ is —$NHR^3$.

Thus, in one aspect, the enone-containing compound is compound 5 where -$ZR^3$ is —$OR^3$, and —$OR^3$ is exclusively or primarily in the beta-configuration, while in another aspect the enone-containing compound is compound 16 where -$ZR^3$ is —$OR^3$, and —$OR^3$ is exclusively or primarily in the beta-configuration.

In a related aspect of the invention, compounds are provided that may be prepared by the oxidation of an enone-group to the corresponding diol functionality, where these compounds are valuable precursors in the preparation of steroids having anti-inflammatory and other therapeutic activity (see, e.g., U.S. Pat. No. 6,046,185) where these compounds have at least hydroxyl or protected hydroxyl groups and are represented by the formula

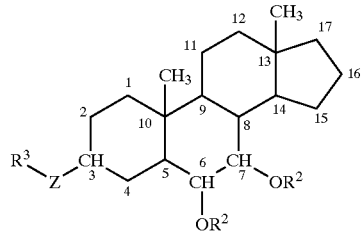

wherein:

Z is O, S or $NR^1$;

each of C1, C2, C4, C11, C12, C15, C16 and C17 is independently substituted with (a) one of: =O, =$C(R^1)(R^1)$, —$C(R^1)(R^1)(C(R^1)(R^1))_n$— and —$(O(C(R^1)(R^1))_nO)$— wherein n ranges from 1 to about 6; or (b) two of the following, which are independently selected: —X, —$R^1$ and —$OR^2$;

each of C5, C8, C9 and C14 is independently substituted with one of —X, —$R^1$ or —$OR^2$;

$R^1$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded; and $R^2$ is H or a protecting group such that —$OR^2$ is a protected hydroxyl group, where vicinal —$OR^2$ groups may together form a cyclic structure which protects vicinal hydroxyl groups, and where geminal —$OR^2$ groups may together form a cyclic structure which protects a carbonyl group;

$R^3$ is benzoyl or substituted benzoyl; and

X is fluoride, chloride, bromide and iodide.

In various aspects of the invention directed to the triol steroids: $R^3$ is nitro-substituted benzoyl; and/or each of C1, C2, C4, C11, C12, C15 and C16 is substituted with two hydrogens; and/or each of C5, C8, C9 and C14 is substituted with one hydrogen; and/or C17 is substituted with a substituent selected from =O, —$(O(C(R^1)(R^1))_nO)$— wherein n ranges from 1 to about 6, hydrogen and —$OR^2$, and two $OR^2$ groups. In another aspect of these embodiments, Z is $NR^1$ where $R^1$ is defined above, and where a preferred $R^1$ is selected from an amino protecting group and H, i.e., $R^1$ in the group —$NR^1$ is preferably $R^3$ so that -$ZR^3$ is $N(R^3)_2$ or H so that -$ZR^3$ is —$NHR^3$.

Thus, in one aspect, the diol-containing steroid compound is a trihydroxy compound having the formula (7)

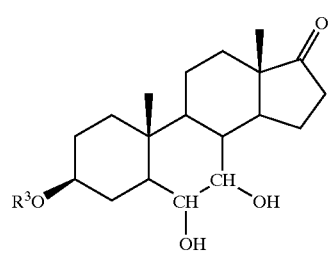

In one aspect, the triol-containing steroid is compound 9 where —$OR^3$ is only or primarily in the beta-configuration, while in another aspect the triol-containing steroid is compound 20 where —$OR^3$ is only or primarily in the beta-configuration, where these compound are identified in the FIGURE and below:

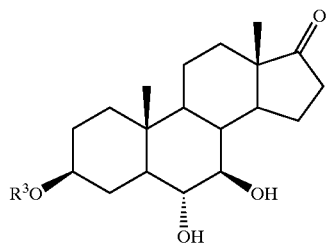

9 $R^3$ = pNO₂Bz
20 $R^3$ = Bz

Compounds of the invention may be prepared as described herein or by synthetic methods analogous to those described in U.S. Pat. No. 6,046,185 (particularly those compounds wherein Z is O or S) or PCT International Publication No. WO 01/83512 (particularly those compounds wherein Z is $NR^1$). Likewise, compound useful in the methods of the invention are known in the art, see, e.g., U.S. Pat. No. 6,046,185 and PCT International Publication No. WO 01/83512.

EXAMPLES

Chemicals and reagents as used in the following Examples were obtained from standard chemical supply houses, and were used without purification unless otherwise noted. Suitable chemical supply houses include Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, the following abbreviations have the indicated meaning: aq. is aqueous; DCM is dichloromethane which may also be referred to as methylene chloride; g is gram(s); HPLC is high pressure (or performance) liquid chromatography; Kg is kilogram(s); L is liter(s); M is molar; mL is milliliter(s); mmol is millimole(s); mol is mole(s); NMR is nuclear magnetic resonance spectroscopy; PMA is phosphomolybdic acid in ethanol (20% wt); THF is tetrahydrofuran; TLC is thin layer chromatography; and UV is ultraviolet radiation. Examples 1 and 2 make reference to compounds having the structures shown in the FIGURE.

Example 1

Allylic Oxidation of Steroid
A. Conversion Compound 2 to Compound 3

Compound 2 (250 g, 0.87 mol, Steraloids, Newport, R.I., USA), 10-camphorsulfonic acid (2.38 g, 10.22 mmol), ethylene glycol (126.13 mL, 2.6 mol) and cyclohexane (1.0 L) were charged to a reaction flask and heated to reflux. The reaction mixture was stirred for 20 hours while water was collected and removed by a Dean-Stark trap. The reaction mixture was allowed to cool to room temperature and filtered through a Buchner funnel. The solid was washed with cyclohexane, water, and aq. $NaHCO_3$ solution (50 mL) to remove any residual ethylene glycol. Residual water was azeotroped out of the solid using toluene to provide compound 3. Yield was 99%.

B. Conversion of Compound 3 to Compound 4

Compound 3 (1.326 Kg, 3.98 mol, prepared as in Example 1, Part A) was dissolved in ethyl acetate (9.5 L) under an argon atmosphere. Pyridine (96.77 mL, 1.19 mol) and triethylamine (111.75 mL, 7.97 mol) were added followed by the slow addition of para-nitrobenzoyl chloride (888.11 g, 4.78 mol). The reaction mixture was stirred for 4 hours. TLC using PMA and UV visualization indicated complete conversion. The reaction mixture was filtered and the solid was set aside. The mother liquor was concentrated by rotary evaporation. Heptane was added to the concentrate to crash out the solid product, which was collected on a Buchner funnel. The solids were combined and washed with water several times to remove the inorganic salts. A cold acetone trituration over a 2 hour time period afforded 1.890 Kg of compound 4 with an HPLC purity of 98.5%. Yield was 98.4%.

C. Conversion of Compound 4 to Compound 5

Acetonitrile (3.75 L) was charged to a 30 L reactor followed by compound 4 (2.5 kg, 5.19 mol, prepared as in Example 1, Part B), dichloromethane (3.75 L), pyridine (2.5 L) and CuI (0.02 kg, 0.105 mol). t-Butyl hydroperoxide (6.70 kg, 51.9 mol) was added and the mixture was agitated at room temperature for 1.0–2.0 hours. The mixture was then heated to 45° C. and stirred until TLC indicated no starting material remained. The mixture was cooled to 10–15° C. then a 33% solution of $Na_2S_2O_3.5H_2O$ (prepared by dissolving 2.5 kg of $Na_2S_2O_3.5H_2O$ in 10.07 mol of water) was added. After agitating the mixture at room temperature for 1.5–2.0 hours, dichloromethane (5.0 L) was added. The layers were separated and the aqueous layer was extracted with dichloromethane (4.0 L). The organic layers were combined and washed with 10% brine solution (8.75 kg), dried with $MgSO_4$ (0.5 kg), filtered and concentrated to remove most of the volatile solvents, and leave a viscous residue. Methanol (2.0 L) was added and the mixture was again concentrated to remove additional volatile solvent. Methanol (7.0 L) was added to the residue and the mixture was agitated at room temperature overnight. The mixture was filtered and the solid was collected and washed with cold methanol. The solid product (compound 5, 62.5% yield) was dried in a vacuum oven at 35–40° C. until no residual solvent was observed by NMR.

Example 2

Allylic Oxidation of Steroid
A. Conversion of Compound 3 to Compound 15

Compound 3 (20.48 g, prepared as described in Example 1, Part A) was dissolved in dichloromethane (60 mL) and pyridine (60 mL) in a 3 neck round bottom flask. The flask was fitted with a condenser and stopper and the mixture was cooled using an ice-bath and stirred under inert atmosphere ($N_2$ gas). Benzoyl chloride (12 mL) was added while maintaining ice-bath temperatures within the reaction flask. The mixture was stirred overnight at room temperature after which TLC indicated that the reaction had proceeded to completion. Dichloromethane (50 mL) and 10% aq. sodium bicarbonate (50 mL) were added and the layers were separated. The aqueous layer was extracted with dichloromethane (50 mL) then the combined organic layers were washed with water (50 mL) then brine solution (50 mL). The organic layer was dried over $MgSO_4$, filtered, and the filtrate was concentrated to dryness. Methanol (30 mL) was added, then the mixture was again concentrated to dryness. A second portion of methanol (80 mL) was added and the resultant slurry was filtered and vacuum dried to yield compound 15 as a white solid (96% yield).

B. Conversion of Compound 15 to Compound 16

Compound 15 (50.06 g, prepared as in Example 2, Part A) was dissolved in acetonitrile (150 mL) and cyclohexane (150 mL), in a three neck round bottom flask, equipped with nitrogen bubbler, condenser tube, overhead stirrer and addition funnel. Pyridine (51 mL) was added using a syringe. CuI (0.44 g) was added followed by t-butyl hydroperoxide (150 mL). The mixture was heated to 40° C. for 0.5 hours. The temperature was monitored until constant then the mixture was warmed to 45° C. The mixture was stirred for 4 hours and then cooled to room temperature. Aq. $Na_2S_2O_3.5H_2O$ (prepared by dissolving 49.76 g $Na_2S_2O_3.5H_2O$ in 250 mL water) was added to the mixture and the mixture was stirred for one hour. The layers were separated and water (250 mL) was added to the aqueous layer which was then extracted with dichloromethane (250 mL). The combined organic layers were washed with water (750 mL), then brine (100 mL). Dichloromethane (350 mL) and acetonitrile (100 mL) were added to break the emulsion and the layers were separated. The organic layer was washed with 10% aq. NaCl (800 mL). The organic layer was dried with $MgSO_4$, filtered and the filtrate was evaporated to dryness. Cold methanol (75 mL) was added and the mixture was agitated at room temperature for 2 hours then cooled using an ice bath for 2 hours. The product was collected by filtration and dried under high vacuum. The procedure on the filtrate was repeated to yield a second crop of product (total yield 35.0 g, 67.7%).

Example 3

Conversion of α,β-Unsaturated Ketone to a Vicinal Diol

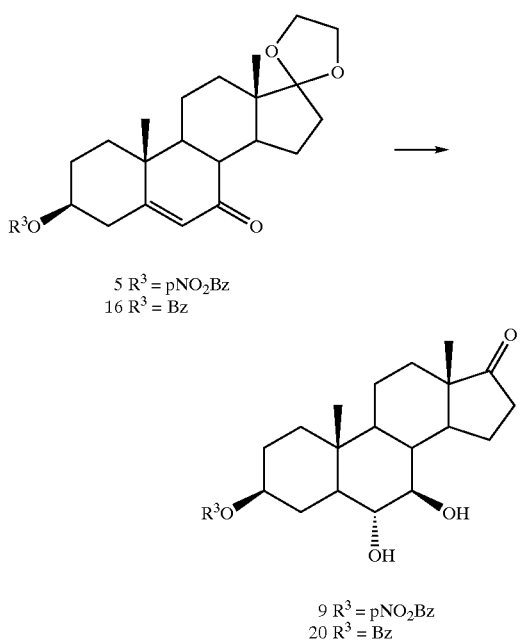

5 R³ = pNO₂Bz
16 R³ = Bz

9 R³ = pNO₂Bz
20 R³ = Bz

A. Conversion of Compound 16 to Compound 20

Compound 16 (4:99 g, prepared as in Example 2, Part B) was dissolved in THF (25 mL) in a 3 neck round bottom flask equipped with nitrogen bubbler, condenser tube, and rubber septum, and the flask contents were agitated for 10 minutes. BH₃/THF (24 mL, 1 M) was added and the mixture was agitated for 2.5 hours. The reaction was monitored by TLC and, upon disappearance of starting material and intermediate, was quenched with water (22 mL). NaBO₃·4H₂O (3.46 g) was added and the mixture was agitated overnight. After the reaction was deemed complete according to TLC, concentrated HCl (2 mL) was added and the mixture was heated to 65° C. until deprotection was complete (approximately 2 hours). The mixture was cooled to room temperature and potassium carbonate was added to achieve a pH of 7–8. The layers were separated and the aqueous layer was extracted with ethyl acetate (30 mL). The combined organic layers were washed with water (40 mL) then 10% aq. NaCl (40 mL). The organic layer was dried with MgSO₄, filtered and concentrated to dryness. Ethyl acetate (10 mL) was added to the residue and the slurry was cooled to −5° C.–0° C. for 2 hours. The solid was filtered and dried under high vacuum to yield the product (compound 20) as an off-white solid (50% yield).

B-1. Conversion of Compound 5 to Compound 9

Compound 5 (prepared as in Example 1, Part C) is converted to compound 9 essentially as described in Example 3, Part A.

B-2. Conversion of Compound 5 to Compound 9

Borane/THF (126 mL) was added to a 500 mL 3-neck reaction flask followed by THF (150 mL), and the solution was cooled to −5–0° C. with ice/acetone bath. Starting material (compound 5, prepared as in Example 1, Part C, 25.0 g) was added in portions (5 portions) to the reaction flask during a 2 hour addition period. The reaction mixture was kept at −5–0° C. until TLC indicated the absence of the starting material. Water (35 mL) was charged slowly to the mixture followed by NaBO₃·4H₂O (19.6 g), and the mixture maintained at room temperature overnight. Concentrated HCl (10 mL) was added and the mixture was heated at 65° C. until no starting material remained (approximately 2 hrs). K₂CO₃ (~4.0 g) was added to adjust the pH to ca. 7.0–8.0, the layers were separated, the aqueous layer was washed with dichloromethane (200 mL), and the organic layers were combined and washed with water (200 mL) followed by 10% NaCl solution (200 mL). The organic layer was dried with MgSO₄, filtered and concentrated to dryness. Ethyl acetate (50 mL) was added to the residue and the mixture was stirred at room temperature overnight. The mixture was filtered and the solid was washed with cold ethyl acetate, and dried under high vacuum to afford 23.7 g of the product (compound 9) (69% yield).

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method comprising:

a) providing a compound of the formula:

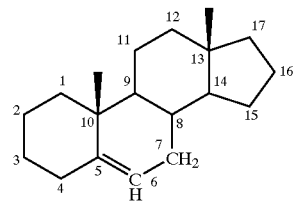

wherein:
each of C1, C2, C4, C11, C12, C15 and C16 is independently substituted with
i) one of: =O, =C(R¹)(R¹), —C(R¹)(R¹)(C(R¹)CR¹))ₙ— and —(O(C(R¹)(R¹))ₙO)— wherein n ranges from 1 to about 6; or
ii) two of the following, which are independently selected: —X, —R¹ and —OR²;
C3 is substituted with hydrogen or -ZR³;
each of C8, C9 and C14 is independently substituted with one of —X, —R¹ or —OR²;
C17 is substituted with two —OR² groups or is a ketal;
R¹ at each occurrence is independently selected from H and C₁₋₃₀ organic moiety that may optionally contain at least one heteroatom selected from the group consisting of boron, halogen, nitrogen, oxygen, silicon and sulfur, where two geminal R¹ groups may together form a ring with the carbon atom to which they are both bonded;
R² is H or a protecting group such that —OR² is a protected hydroxyl group, where vicinal —OR² groups may together form a cyclic structure which protects vicinal hydroxyl groups, and where geminal —OR² groups may together form a cyclic structure which protects a carbonyl group, with the proviso that either or both of —OR² at C6 and C7 represents a carbonyl or protected carbonyl group;
R³ is benzoyl or substituted benzoyl;

X represents fluoride, chloride, bromide and iodide; and
Z is selected from O, S and $NR^1$;
b) contacting the compound with reagents comprising copper iodide and t-butyl hydroperoxide to provide a mixture; and
c) maintaining the mixture of step b) under oxidizing conditions to convert to compound to a product having a carbon skeleton and an α,β-unsaturated ketone moiety as present in formula (4)

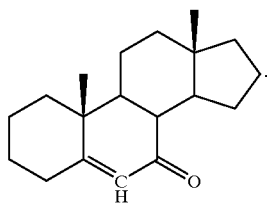

(4)

2. The method of claim 1 wherein the reagents further comprise an amine.

3. The method of claim 2 wherein the amine is pyridine.

4. The method of claim 1 wherein C1, C2, C4, C11, C12, C15 and C16 are substituted with two hydrogens, and C8, C9 and C14 are substituted with one hydrogen.

5. The method of claim 1 wherein C3 is substituted with hydrogen and $-OR^3$.

6. The method of claim 1 wherein the product has the formula

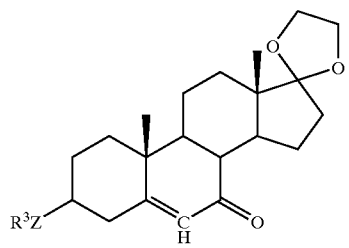

wherein Z is selected from O, S and $NR^1$, $R^3$ is benzoyl or substituted benzoyl, and except functionality shown in the structure, each carbon is fully substituted with hydrogen.

7. The method of 6 wherein $R^3$ is para-nitrobenzoyl and $-ZR^3$ is exclusively or primarily in the β-configuration.

8. The method of claim 6 wherein $R^3$ is benzoyl and $-ZR^3$ is exclusively or primarily in the β-configuration.

9. The method of claim 1 wherein Z is O.

10. The method of claim 1 wherein Z is S.

11. The method of claim 1 wherein Z is $NR^1$.

12. A method comprising
a) providing a compound of the formula:

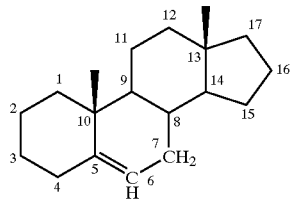

wherein:
each of C1, C2, C4, C11, C12, C15 and C16 is independently substituted with i) one of: $=O$, $=C(R^1)(R^1)$, $-C(R^1)(R^1)(C(R^1)(R^1))_n-$ and $-(O(C(R^1)(R^1))_nO)-$ wherein n ranges from 1 to about 6; or
ii) two of the following, which are independently selected: $-X$, $-R^1$ and $-OR^2$;

C3 is substituted with hydrogen or $-ZR^3$;

each of C8, C9 and C14 is independently substituted with one of $-X$, $-R^1$ or $-OR^2$;

C17 is substituted with two $-OR^2$ groups or is a ketal;

$R^1$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded;

$R^2$ is H or a protecting group such that $-OR^2$ is a protected hydroxyl group, where vicinal $-OR^2$ groups may together form a cyclic structure which protects vicinal hydroxyl groups, and where geminal $-OR^2$ groups may together form a cyclic structure which protects a carbonyl group, with the proviso that either or both of $-OR^2$ at C6 and C7 represents a carbonyl or protected carbonyl group;

$R^3$ is benzoyl or substituted benzoyl;

X represents fluoride, chloride, bromide and iodide; and

Z is selected from O, S and $NR^1$;

b) contacting the compound with reagents comprising an oxidizing agent and an amine to provide a mixture; and c) maintaining the mixture of step b) under oxidizing conditions to convert the compound to a product having a carbon skeleton end an α,β-unsaturated ketone moiety as present in formula (4)

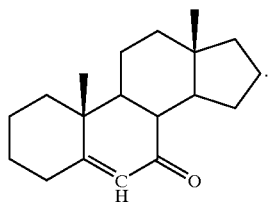

(4)

13. The method of claim 12 wherein the oxidizing agent is copper iodide and t-butyl hydroperoxide.

14. The method of claim 12 wherein the amine is pyridine.

15. The method of claim 12 wherein C1, C2, C4, C11, C12, C15 and C16 are substituted with two hydrogens, and C8, C9 and C14 are substituted with one hydrogen.

16. The method of claim 12 wherein C3 is substituted with hydrogen and $-OR^3$.

17. The method of claim 12 wherein the compound has the formula wherein Z is selected from O, S and $NR^1$, $R^3$ is benzyl or substituted benzoyl and, except for functionality shown in the structure, each carbon is fully substituted with hydrogen.

18. The method of claim 17, wherein $R^3$ is *para*-nitrobenzoyl and $-Zr^3$ exclusively or primarily in the β-configuration.

19. The method of claim 17, wherein $R^3$ is benzoyl and $-ZR^3$ is exclusively or primarily in the β-configuration.

20. The method of any one of claims 17–19 wherein Z is O.

* * * * *

UNITED STATES PATENT AND TRADEMARK OFFICE
CERTIFICATE OF CORRECTION

PATENT NO. : 6,982,329 B2
APPLICATION NO. : 10/744857
DATED : January 3, 2006
INVENTOR(S) : David L. Burgoyne et al.

It is certified that error appears in the above-identified patent and that said Letters Patent is hereby corrected as shown below:

Column 22
Line 44, "CR$^1$))$_n$" should read as -- (R$^1$))$_n$ --

Column 23
Line 7, "to" should read as -- the --
Line 46, "of 6" should read as -- of claim 6 --

Column 24
Line 33, "end" should read as -- and --
Line 55, the following should be inserted following the word "formula"

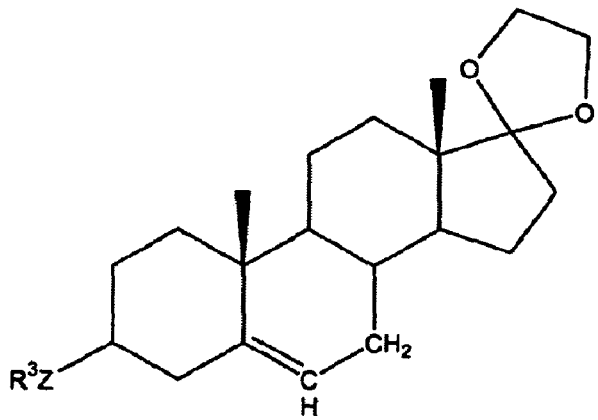

Signed and Sealed this

Third Day of October, 2006

JON W. DUDAS
*Director of the United States Patent and Trademark Office*